United States Patent [19]
Tuomela et al.

[11] Patent Number: 5,817,924
[45] Date of Patent: Oct. 6, 1998

[54] METHOD AND APPARATUS FOR MEASURING OXYGEN TRANSMISSION THROUGH CONTACT LENSES

[75] Inventors: Stephen D. Tuomela, Oakdale; Joel A. Fischer, St. Paul, both of Minn.

[73] Assignee: Modern Controls, Inc., Minneapolis, Minn.

[21] Appl. No.: 10,240

[22] Filed: Jan. 21, 1998

[51] Int. Cl.$^6$ .............................. G01N 15/08; G02C 7/04
[52] U.S. Cl. ............................................ 73/38; 351/160 R
[58] Field of Search ........................ 73/38, 865.9, 865.6; 351/160 R, 160 H

[56] References Cited

U.S. PATENT DOCUMENTS 3,228,741  1/1966  Becker ................................. 351/160 R

*Primary Examiner*—Michael Brock
*Assistant Examiner*—Jay L. Politzer
*Attorney, Agent, or Firm*—Palmatier, Sjoquist, Voigt & Christensen, P.A.

[57] ABSTRACT

An apparatus for measuring the gas transmission rate through contact lens material, and a method of measuring, using a test cell having an upper and lower gas chamber and separating the upper and lower chamber with a layered group of films, including a contact lens film material clamped between an upper and lower guard film, and flowing oxygen through the upper chamber and an inert gas through the lower chamber, the lower chamber being connected to a coulometric sensor to measure oxygen content in the inert gas at defined intervals, to obtain a first series of oxygen transmission rates. A second series of oxygen transmission rates are made with the same apparatus, but with the contact lens material removed from the apparatus, and the transmission rate through the contact lens material is calculated by subtracting the reciprocal of the second measured transmission rate from the reciprocal of the first measured transmission rate, then taking the reciprocal of the difference.

8 Claims, 2 Drawing Sheets

METHOD AND APPARATUS FOR MEASURING OXYGEN TRANSMISSION THROUGH CONTACT LENSES

BACKGROUND OF THE INVENTION

The present invention relates to a method and apparatus for measuring the transmission rate of oxygen through contact lenses. Oxygen transmission through contact lenses has been considered to be a very important factor in the comfort and safety of the user who wears contact lenses. If the contact lens material does not permit a sufficient permeation of oxygen, the eye of the user can become infected or irritated, leading to severe physical problems for the user.

The accurate measurement of oxygen transmission rate through contact lens material is seriously handicapped by the effect of relative humidity on such measurements. The transmission rate through some lenses can change by one hundred percent or more with a change of one-half percent relative humidity, especially at high values of relative humidity which are encountered in actual use of the lenses. Thus, controlling relative humidity at 99 percent, versus say 99.5 percent, becomes a very difficult task while attempting to make accurate oxygen transmission measurements.

Relative humidity is also affected by the type of saline solution in which the contact lens is immersed, because the saline solution determines the vapor pressure at the contact lens surface, and the vapor pressure determines the relative humidity at the lens surface. The definition of relative humidity, taken from the *Handbook of Chemistry and Physics*, 39th edition (1957–58), is "the ratio of the quantity of water vapor present in the atmosphere to the quantity which would saturate at the existing temperature." It is also the ratio of the pressure of water vapor present to the pressure of saturated water vapor at the same temperature. The saturated water vapor pressure at any given temperature can be found by reference to the *Handbook of Chemistry and Physics*. The water vapor pressure above any particular aqueous solution can be determined in a number of ways, including the following two-step procedure:

1) measure the concentration of the solution by measuring the index of refraction with a refractometer, as described in *Experiments in Physical Chemistry and Physics*, 5th edition, Shoemaker, Garland and Nibler;

2) look up the water vapor pressure for that solution concentration in the *Handbook of Chemistry and Physics* or the *International Critical Tables*.

Once the saturated water vapor pressure ($WVP_{saturated}$) and the solution water vapor pressure ($WVP_{present}$) are known, the relative humidity in percentage (RH%) can be determined from the following expression:

$$RH\% = WVP_{present}/WVP_{saturated}$$

It is commonly acknowledged that the water content of hydrogel contact lenses impacts the oxygen transmission rate through the material. However, measuring the water content of various hydrogel contact lens materials is itself a very difficult problem, being affected by the relative humidity conditions of the lens environment. One paper which describes the problems of water content measurements is entitled "Humidity-Conditioned Gravimetric Method to Measure the Water Content of Hydrogel Contact Lens Materials", by Galas and Enns, and published in the Journal of Optometry and Vision Science, Volume 70, No. 7, pp. 577–586 (1993). This paper describes two techniques of measuring the water content of hydrophilic soft contact lens materials—refractive index and gravimetry. Both techniques are subject to inaccuracies in the measurement properties.

A second paper describes a coulometric method of measuring oxygen transmission, and is entitled "Coulometric Method for Measuring Oxygen Flux and Dk of Contact Lenses and Lens Materials", by Winterton, White and Kai C. Su, and published in "International Contact Lens Clinic Journal", Volume 14, Number 11 (November 1987). This paper describes a test setup which attempts to control all environmental factors associated with making accurate oxygen measurements, but the test fixtures and techniques are necessarily quite complex. The paper does describe the use of a coulometric oxygen sensor for making oxygen measurements, which is the same device used with the present invention.

It is an object of the present invention to provide a test apparatus which enables the precise and repeatable measurement of oxygen transmission rate through a contact lens material, or similar type material, under controlled relative humidity conditions.

It is a further object of the present invention to provide a method of measuring oxygen transmission rate through contact lens material, or similar material, by a first and second series of comparative measurements taken with and without the contact lens material.

SUMMARY OF THE INVENTION

The apparatus of the invention includes a test fixture which is arranged as a gas cell having two halves, with a group of test components tightly clamped between the two cell halves, thereby forming a gas chamber above and below the group of test cell components. A gas inlet and gas outlet is provided in each of the cell halves. The test cell components multiple layers comprising an upper contact mounting plate, an upper guard film, a sample of contact lens material with a droplet of saline solution applied, a lower guard film, and a lower contact mounting plate.

The method of the present invention comprises the first steps of measuring the oxygen transmission rate from one gas chamber to the other, through the layered test components, and then measuring the second steps of measuring the oxygen transmission rate from one gas chamber to the other, with the intermediate contact lens material removed. The transmission rate of oxygen through the contact lens material is then calculated using an equation of the form $$1/tr_c - 1/tr_{tot} - 1/tr_g$$

where the term $tr_c$ is the transmission rate of oxygen through the contact lens material, the term $tr_{tot}$ is the transmission rate of oxygen through all of the layers as determined by the first steps of measuring, and the term $tr_g$ is the transmission rate of oxygen through the layers as determined by the second steps of measuring.

The foregoing and other objects and advantages will become apparent from the following detailed description and claims, and with reference to the appended drawings.

DESCRIPTION OF THE PREFERRED EMBODIMENT

If a film (a) transmits a known quantity of oxygen, we know that if there is another film (b) of the same material, but twice as thick, the film (b) will have one-half the transmission rate of the film (a). The same thing can be said about two films (a) and (b) having identical characteristics and thicknesses; if you mount films (a) and (b) one on top of the other in a test chamber, the resulting measured transmission rate of the two together will be one-half of the transmission rate of film (a) alone. This can be expressed mathematically as $$1/tr_{tot} = 1/tr_a + 1/tr_b$$

This same mathematical expression can be used for multiple layers of film, where each film has any transmission rate value. For example, for five different films (a), (b), (c), (d) and (e), the transmission rate through all of them layered together is $$1/tr_{tot} = 1/tr_a + 1/tr_b + 1/tr_c + 1/tr_d + 1/tr_e$$

If it is desired to know the transmission rate through film (e) alone, it can be determined by indirect measurement, first measuring the transmission rate through all five films layered together (abcde), and then removing film (e) and repeating the measurements of the remaining four films (abcd) layered together. The transmission rate through film (e) can then be derived by the equation $$1/tr_e = 1/tr_{abcde} - 1/tr_{abcd};$$

where $1/tr_{abcde}$ is obtained from the first series of test cell measurements and $1/tr_{abcd}$ is obtained from the second series of test cell measurements.

The foregoing method can be applied for the measurement of oxygen transmission rate through contact lens materials, or other similar materials, by constructing the test setup so as to place the contact lens material as one of the layers described above. Of course, in any case, it is critical that the test conditions, particularly relative humidity, be carefully controlled to be identical in both sets of measurements, so that the vapor pressure on both sides of the contact lens material is known or controlled. Likewise, the relative humidity in the intermediate region between the two films remaining after the contact lens material has been removed for the second set of test measurements must be controlled to be the same as the relative humidity of the region when the first set of test measurements are taken. This problem is solved in the present invention by applying a droplet of saline solution above and below the contact lens material during the first set of test measurements, and also applying a droplet of the same saline solution to the intermediate region between film layers when the contact lens material is removed for the second set of test measurements. The vapor pressure of the saline material is known through reference to an appropriate technical table, or it can be measured by well known techniques, to ensure that the relative humidity can be controlled.

Figure 1:
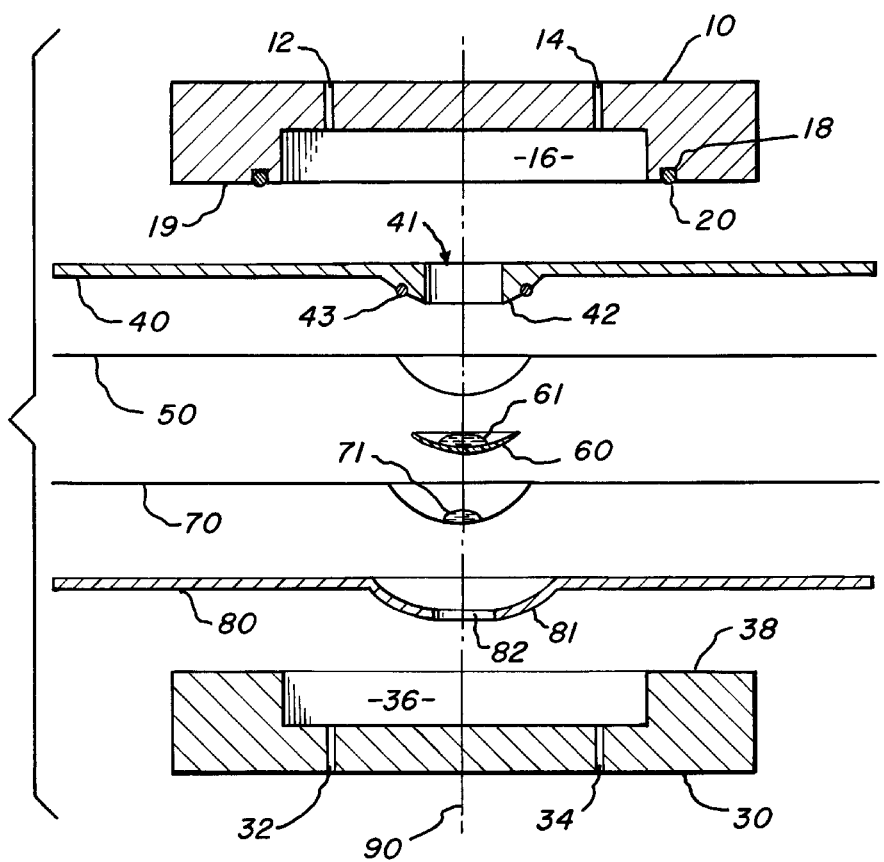
FIG. 1 shows an exploded view of the apparatus test setup for making a first set of measurements.

FIG. 1 shows the test setup of the present invention in exploded view. An upper test cell housing 10, generally circular in top view, has a gas inlet 12 and a gas outlet 14, each having passages to a lower recess which will form an upper gas chamber 16 when the test setup is fully assembled.

A circular groove 18 is preferably formed in the lower surface of housing 10, and an O-ring 20 is seated in the groove 18. A lower test cell housing 30, also generally circular in construction, has a gas inlet 32 and a gas outlet 34, each having passages to a recess which will form a lower chamber 36 when the test setup is fully assembled. The upper surface 38 of housing 30 is smoothly formed to tightly seal against the layers which are positioned between the upper surface 38 and the lower surface 19 of housing 10, and the topmost layer tightly engages O-ring 20 when the test setup is fully assembled and the housing halves are clamped together.

Multiple layers of test components are positioned between upper housing 10 and lower housing 30. A topmost layer is formed by an upper contact mounting plate 40, which is in the shape of a circular plate having a central opening 41 aligned about axis 90, with a lower, generally spherical, shoulder 42 surrounding opening 41. An O-ring 43 is preferably positioned in a circular groove in shoulder 42 to ensure a tight seal between shoulder 42 and the next lower layer. The upper contact mounting plate 40 may be made from a fairly rigid material such as stainless steel.

The layer next below upper contact mounting plate 40 is an upper guard film 50, preferably formed of a material capable of transmitting oxygen therethrough at least as rapidly as the contact lens material to be tested. A plastic material such as Teflon® is satisfactory for most purposes because it has a very high oxygen transmission rate and it will maintain water in a saline solution; i.e, it is a very good water barrier material. Also, the center portion of the upper guard film 50 must be deformable to conform to the spherical surface area of the upper contact mounting plate 40.

The next lower layer is the contact lens material 60, which is centrally positioned beneath the upper guard film 50 and in alignment with opening 41. A droplet of saline solution 61 is applied to the upper surface of contact lens material 60 to thoroughly wet the contact lens material and to provide a known relative humidity in the region between the contact lens material 60 and the upper guard film 40.

A lower guard film 70 is positioned beneath the contact lens material 60, and a droplet of saline solution 71 is applied to the upper surface of lower guard film 70, for the same reason as described above with reference to droplet 61; ie, to thoroughly wet the contact lens material 60 and to provide a known relative humidity in the region between contact lens material 60 and lower guard film 70. The material selected for lower guard film 70 is preferably Teflon®, for the same reasons as earlier described.

A lower contact mounting plate 80 is positioned beneath lower guard film 70, having a central spherical shape 81 generally conforming to the spherical shape of shoulder 42. An opening 82 is formed at the central axis 90, in alignment with opening 41 of upper contact mounting plate 40.

Figure 2:
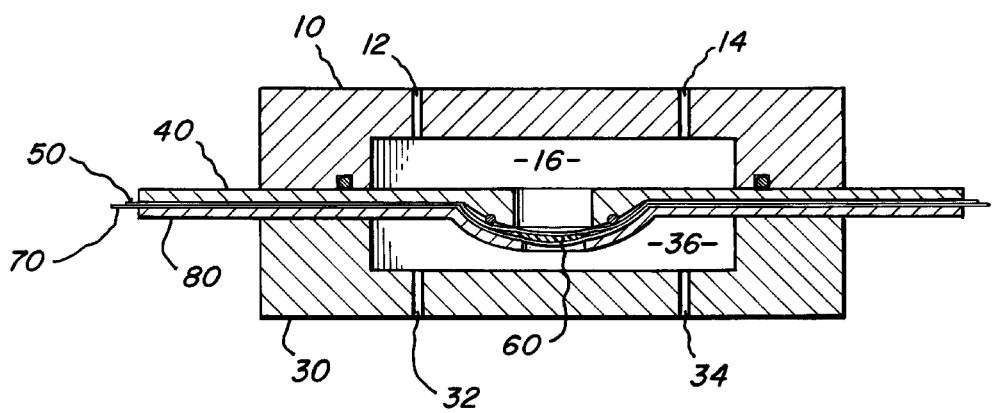
FIG. 2 shows the apparatus of FIG. 1 in a closed position for conducting test measurements.

FIG. 2 shows the test setup of FIG. 1 in fully assembled form, with the multiple layers tightly clamped between housing 10 and housing 30. An external clamping device (not shown) may be used to ensure a tight seal between the various components. In the position illustrated, the contact lens material 60 is tightly held between the upper and lower guard films 50 and 70, and the saline solution droplets 61 and 71 are contained in the respective regions between the layers.

Figure 3:
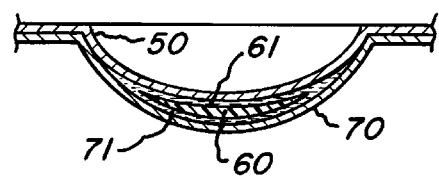
FIG. 3 shows an enlarged view of a portion of the film layers of FIG. 2.

FIG. 3 shows an expanded portion of FIG. 2, illustrating the layered relationship of upper guard film 50, contact lens material 60, and lower guard film 70, with droplets 61 and 71 dispersed intermediate the layers.

The transmission rate ($tr_{60}$) of the contact lens material 60, plus the transmission rate ($tr_{50}$) of the guard film 50, plus the transmission rate ($tr_{70}$) of the guard film 70 can be expressed in terms of the overall transmission rate ($tr_1$) measured through the layered materials according to a first series of measurement steps, described as follows. A source of nitrogen gas, or other inert gas, is connected to inlet 32, and outlet 34 is connected to a coulometric sensor of the type commonly manufactured by the assignee of the present invention. A source of oxygen gas is connected to inlet 12, and outlet 14 is connected to an exhaust port. The lower chamber 36 is purged of any residual oxygen content by flowing nitrogen gas through the chamber before any test measurements are made. A steady flow of oxygen is then introduced into chamber 16, and a steady flow of nitrogen is introduced through chamber 36 and the coulometric sensor connected thereto. The coulometric sensor will generate electrical signals proportionate to and representative of the oxygen detected by the sensor, and a series of these measurements may be assembled in terms of oxygen per unit of time per square cross-section of the exposed layered materials, thus yielding the transmission rate ($tr_1$) through the total layered combination of films 50, 60 and 70.

Figure 4:
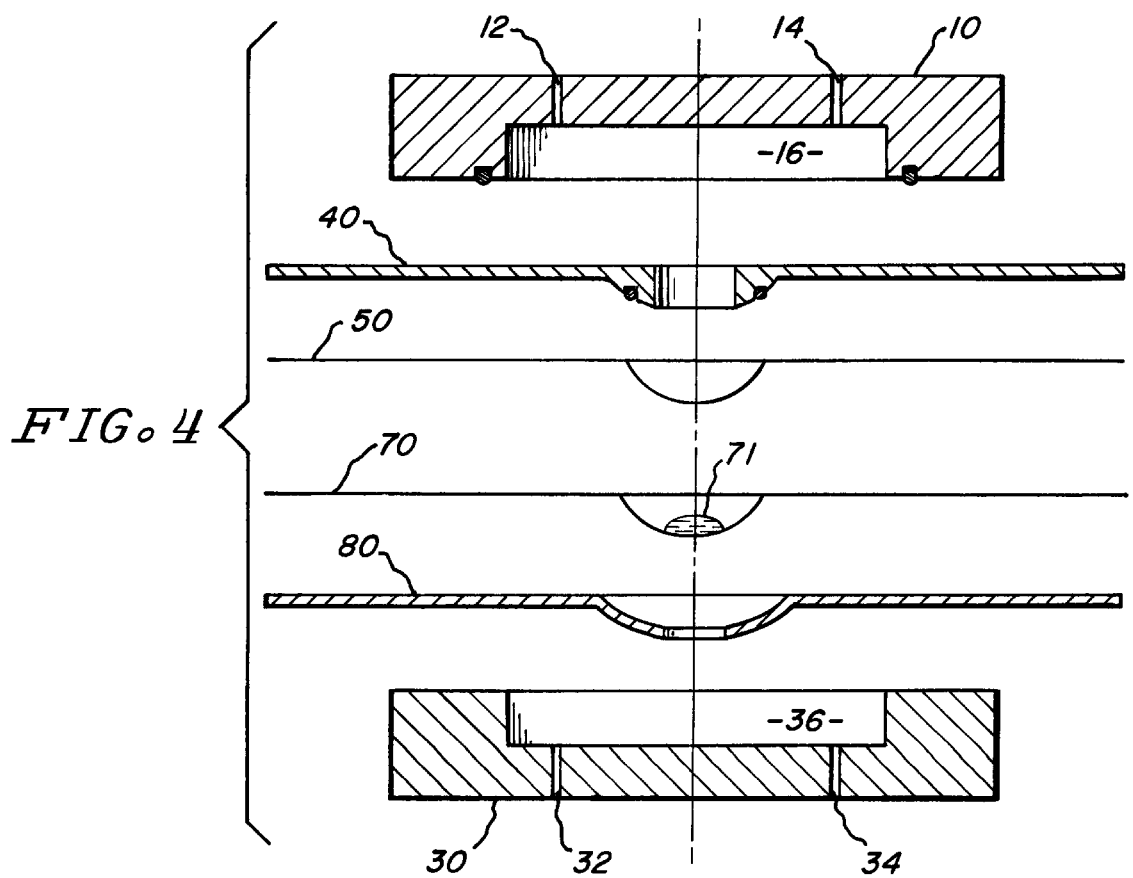
FIG. 4 shows an exploded view of the apparatus test setup for making a second series of test measurements.

Next, the test setup is disassembled, and reassembled without the contact lens material, as is shown in exploded view in FIG. 4. After clamping the housing sections 10 and 30 together, with the layers 40, 50, 70 and 80 clamped therebetween, the lower chamber 36 is again purged of residual oxygen by flowing nitrogen through the chamber. A second series of oxygen measurements is then made by the sensor, and a second transmission rate ($tr_2$) is then determined for the second layered combination. The transmission rate through the contact lens material may then be calculated from the equation $$1/tr_{60} = 1/tr_1 - 1/tr_2$$

The foregoing described apparatus and method has been adapted for use and operation with a test instrument manufactured by the assignee of the present invention, commercially available under the model designation of Mocon Ox-Tran system. The components described herein, and the method of operating the system to obtain the measurements described herein, can readily be accommodated to this system.

The foregoing description of a preferred embodiment of the invention is intended to be illustrative and not limiting. The true scope of the invention is to be understood and limited by the claims herein, variations in particular details of the invention being entirely possible within the overall scope of the invention as claimed.

What is claimed is:

1. An apparatus for measuring the transmission rate of oxygen through a contact lens material, comprising
   a) test cell formed into two separable chamber halves, each half hating a gas inlet and gas outlet, and means for clamping the two halves together:
   b) an upper and lower contact mounting plate adapted for clamping between said two halves; said upper and lower contact mounting plate each having a central opening;
   c) an upper guard film and a lower guard film, respectively clamped between said upper and lower contact mounting plates and
   d) means for removably clamping a contact lens material between said upper and lower guard films, wherein said contact lens material is at least partially aligned with said central openings of said upper and lower contact mounting plates, and the layered combination of the upper guard film, contact lens material, and lower guard film form a barrier between the upper chamber half and the lower chamber half.

2. The apparatus of claim 1, further comprising a saline solution on both sides of said contact lens material in the region of said contact lens material aligned with said central openings.

3. The apparatus of claim 1, wherein said upper contact mounting plate further comprises a semispherical region about said central opening facing toward said guard films, and said lower contact mounting plate further comprises a semispherical region about said central opening facing away from said guard films.

4. An apparatus for separating a gas test cell into two chambers for the purpose of measuring oxygen transmission through contact lens material, comprising:
   a) an upper contact mounting plate made from relatively impermeable material and having a central opening therethrough;
   b) an upper guard film having a known relatively high permeability to oxygen clamped adjacent to said upper contact plate, and bridging said central opening;
   c) said contact lens material clamped adjacent said upper guard film material, and bridging said central opening;
   d) a lower guard film having a known relatively high permeability to oxygen clamped adjacent to said contact lens material, and bridging said central opening; and
   e) a lower contact mounting plate made from relatively impermeable material and having a central opening therethrough in alignment with said upper contact mounting plate central opening;
   whereby said upper guard film, contact lens material, and lower guard film form layers separating said test cell into two chambers.

5. The apparatus of claim 4, wherein the oxygen transmission rate through said upper guard film and said lower guard film is at least as great as the oxygen transmission rate through said contact lens material.

6. The apparatus of claim 4, further comprising a saline solution intermediate said contact lens material and said upper guard film, and intermediate said contact lens material and said lower guard film.

7. A method of measuring the transmission rate of oxygen through a contact lens material, comprising the steps of:
   a) clamping said contact lens material intermediate a pair of guard films in a test cell having an upper gas flow chamber above said contact lens material and a lower gas flow chamber below said contact lens material;
   b) flowing an oxygen gas through said upper gas flow chamber and an inert gas through said lower gas flow chamber, and connecting said lower gas flow chamber to a coulometric sensor;
   c) measuring the oxygen flow through the combination of said upper and lower guard films and said contact lens material with said coulometric sensor, and calculating the transmission rate ($tr_1$) of said oxygen flow;
   d) removing said contact lens material from said test cell and reconstructing said cell with only said upper and lower guard film;
   e) flowing an oxygen gas through said upper gas flow chamber and an inert gas through said lower gas flow chamber, and connecting said lower gas flow chamber to a coulometric sensor;
   f) measuring the oxygen flow through the combination of said upper and lower guard films with said coulometric sensor, and calculating the transmission rate ($tr_2$) of said oxygen flow; and g) calculating the transmission rate ($tr_c$) of oxygen flow through said contact lens material by the expression $$1/tr_c = 1/tr_1 - 1/tr_2.$$

8. The method of claim 7, further comprising the preliminary steps of applying a droplet of saline solution to both sides of said contact lens material before clamping same according to step a).

* * * * *

UNITED STATES PATENT AND TRADEMARK OFFICE
CERTIFICATE OF CORRECTION

PATENT NO. : 5,817,924
DATED : October 6, 1998
INVENTOR(S) : Stephen D. Tuomela, Joel A. Fischer It is certified that error appears in the above-indentified patent and that said Letters Patent is hereby corrected as shown below:

Claim 1, column 5, line 54, "hating" should be -- having --.

Signed and Sealed this

Second Day of March, 1999

Attest:

Q. TODD DICKINSON

*Attesting Officer*   *Acting Commissioner of Patents and Trademarks*